United States Patent [19]

Robins et al.

[11] 4,056,674

[45] Nov. 1, 1977

[54] DERIVATIVES OF 3-DEAZAGUANINE

[75] Inventors: Roland K. Robins, Santa Ana; Robert J. Rousseau, Laguna Niguel; Abdul M. Mian, Los Angeles, all of Calif.

[73] Assignee: ICN Pharmaceuticals, Inc., Irvine, Calif.

[21] Appl. No.: 584,215

[22] Filed: June 5, 1975

Related U.S. Application Data

[63] Continuation-in-part of Ser. No. 377,078, July 6, 1973, Pat. No. 3,896,135, and a continuation-in-part of Ser. No. 377,079, July 6, 1973, Pat. No. 3,919,193.

[51] Int. Cl.² .................... C07H 19/06; C07H 19/10; C07H 19/16; C07H 19/20
[52] U.S. Cl. .................... 536/28; 260/296 H; 424/180; 536/23; 536/24; 536/29; 548/343
[58] Field of Search .................... 260/211.5 R; 536/23, 536/24, 28, 29

[56] References Cited

U.S. PATENT DOCUMENTS

| | | | |
|---|---|---|---|
| 3,332,935 | 7/1967 | Yamazaki et al. | 260/211.5 R |
| 3,454,559 | 7/1969 | Yamazaki et al. | 260/211.5 R |
| 3,535,207 | 10/1970 | Shiro et al. | 260/211.5 R |
| 3,893,998 | 7/1975 | Secrist et al. | 260/211.5 R |
| 3,917,583 | 11/1975 | Meyer et al. | 260/211.5 R |
| 3,919,193 | 11/1975 | Mian et al. | 260/211.5 R |

OTHER PUBLICATIONS

Cook et al., "Jour. Amer. Chem. Soc.", vol. 97, 1975, pp. 2916–2917.

*Primary Examiner*—Johnnie R. Brown
*Attorney, Agent, or Firm*—Kay H. Boswell

[57] ABSTRACT

Ribofuranosyl derivatives of 3-deazaguanine including the 5'-phosphate, 3',5'-cyclic phosphate and 5'-deoxy, useful as antiviral agents and antibacterial agents, are disclosed.

14 Claims, No Drawings

DERIVATIVES OF 3-DEAZAGUANINE

CROSS-REFERENCE TO RELATED APPLICATIONS

This is a continuation-in-part of our applications Ser. Nos. 377,078 and 377,079 both filed July 6, 1973 now U.S. Pat. No. 3,896,135 and 3,919,193, respectively. The disclosure of those applications is hereby expressly incorporated herein by reference.

BACKGROUND OF THE INVENTION

During the past decade, many nucleoside analogs have been found to the exhibit good antitumor and antiviral activities. Among the presently known synthetic nucleosidic antiviral agents, the more important generally are considered to be 5-iodo-2'-deoxyuridine (IDU), 9-β-D-arabino furanosyladenine (ara-A) and 1-β-D-arabinofuranosylcytosine (ara-C). These compounds, however, are only active against a limited spectrum of viruses which does not include those causing respiratory diseases such as influenza in man. The only nucleosidic analog of which we are aware that is active against these respiratory disease viruses is 1-β-D-ribofuranosyl-1,2,4-triazole-3-carboxamide which is described in U.S. PAT. No. 3,798,209 entitled 1,2,4-Triazole Nucleosides and assigned to the same assignee as this application.

Certain derivatives of this latter compound have also been found to have significant antiviral activity, as have the triazole bases, 1,2,4-triazole-3-carboxamide and 1,2,4-triazole-3thiocarboxamide. Even with the advent of such compounds, however, and the discovery of their antiviral efficacy, there remains a need for compounds which are capable of inhibiting effectively virus infections, especially respiratory disease viruses.

Moreover, when nucleosidic analogs are uses to inhibit either viral or tumor growth, the nucleosides are in vivo metabolized to their corresponding mono or poly phosphates, which are the actual inhibitors of such growth. A major obstacle in the use of nucleoside analogs in chemotherapy, however, is the emergence of cellular resistance to such compounds, as the invasive cells exhibit a low level of kinase or pyrophosphorylase activity and consequently do not produce effective inhibitors. While this problem might be overcome by utilizing nucleoside phosphates, such derivatives often fail to pass through the cellular membrane or are rapidly degraded in the intercellular fluid and thus are ineffective as inhibitors.

In view of the foregoing considerations, it is clearly desirable to have a nucleosidic analog which is capable of effectively inhibiting the development of virus infections and which also possesses superior solubility than presently known antiviral agents. To provide such a compound, however, which not only has acceptable activity but is also capable of penetrating the cellular membrane and contacting the virus infection in effective concentrations, is exceedingly difficult.

SUMMARY OF THE INVENTION

The present invention is directed to derivatives and precursors of 6-amino-1-β-D-ribofuranosylimidazo[4,5-c]pyridin-4(5H) one and 6-amino-3-β-D-ribofuranosylimidazo[4,5-c]pyridin-4(5H)one. The 1 or 3-substituent of the heterocycle may be an acylated, phosphorylated or cyclic phosphorylated sugar or be a deoxysugar or a tetrahydropyranyl group and the heterocyclic substituent may be on either the α of β position of the sugar. The basic heterocyclic moiety may contain either the 6-amino-imidazo[4,5-c]pyridin-4(5H)one ring system or a 4,5-substituted imidazole ring. The acylated, phosphorylated or deoxy position of the sugar moiety may be on the 2',3' or 5'-position or any combination thereof.

A more preferred group of compounds are of the structure

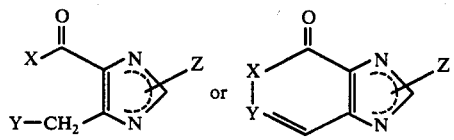

wherein X is

—NH₂ or —OCH₃; Y is

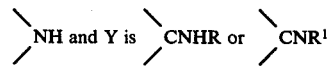

or —C≡N where R is H or acyl and R¹ is =CH—N(CH₃)₂; Z is tetrahydropyranyl, β-D-ribofuranosyl, 5-deoxy-β-D-ribofuranosyl, β-D-ribofuranosyl-5-phosphate, β-D-ribofuranosyl-3,5-cyclic phosphate, C₁–C₁₈ acyl and isopropylidene β-D-ribofuranosyl, C₁–C₁₈ acyl and isopropylidene 5-deoxy-β-D-ribofuranosyl, C₁–C₁₈ acyl and isopropylidene β-D-ribofuranosyl-5-phosphate or C₁–C₁₈ β-D-ribofuranosyl-3,5-cyclic phosphate; and the physiologically acceptable salts thereof; with the proviso that X is

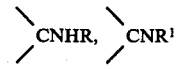

NH and Y is CNHR or CNR¹ only when X and Y are joined together; and X is —NH₂ or —OCH₃ is —C≡N only when X and Y are not joined together; and Z is not β-D-ribofuranosyl or C₁–C₁₈ acyl β-D-ribofuranosyl when Y is

where R is H.

The compounds of the invention are useful as antiviral and anti-bacterial agents.

DETAILED DESCRIPTION OF THE INVENTION

The compounds of this invention may be prepared in accordance with the following schematic representation, as set forth in the illustrative examples which are also follow, in which temperatures and melting points are expressed in degrees Centigrade. Melting points were determined with a Thomas-Hoover capillary melting point apparatus and are uncorrected. Specific rotations were measured in a 1-dm tube with a Perkin-Elmer Model 141 automatic digital readout polarimeter. Proton magnetic resonance (pmr) spectra were obtained on a Varian A-60 spectrophotometer and a Hitachi R-20A spectrophotometer in DMSO-$d_6$ using DSS as an internal reference. Ultraviolet spectra were recorded on a Cary Model 15 spectrometer and infrared spectra on a Perkin-Elmer 257 spectrophotometer (KBr pellets). Elemental analyses were performed by Galbraith Laboratories, Inc., Knoxville, Tenn. Evaporations were carried out under reduced pressure with bath temperature below 40°. Detection of components on silica gel (ICN, Woelm F254) was by ultraviolet light and with 10% sulfuric acid in methanol spray followed by heating.

Acceptable acid addition salts of the basic moiety can be selected from, but not necessarily limited to, the group consisting of hydrochloride, hydrobromide, hydroiodide, citrate, sulfate, substituted sulfate, phosphate, carbonate, bicarbonate and formate. Acceptable salts of the phosphate moiety can be selected from, but not necessarily limited to, the group consisting of alkali and alkaline earths, e.g., sodium, potassium, calcium, magnesium, lithium; ammonium and substituted ammonium, trialkylammonium, dialkylammonium, alkylammonium, e.g., triethylammonium, trimethylammonium, diethylammonium, octylammonium, cetyltrimethylammonium, cetylpyridium.

The hydroxyl groups on the glycon and the amino group of the heterocycle can be blocked with groups such as, but not necessarily limited to, acyl, isopropylidene and dimethylaminomethylene. The acyl group can be selected from a group consisting of straight chain, branched chain, substituted, unsaturated, saturated or aromatic acid such as, but not necessarily limited to, acetic, trifluoroacetic, propionic, n-butyric, isobutyric, valeric, caproic, pelargonic, enanthic, capyrlic, latic, acrylic, propargylic, palmitic, benzoic, phthalic, salicyclic, cinnamic and naphthoic acids.

Following the general procedures and process taught in applicants application Serial Nos. 377,078 and 377,079, methyl 5(4)cyanomethylimidazole-4-(5)-carboxylate (Compound 1) may be prepared and converted into 6-amino-1-β-D-ribofuranosylimidazo[4,5-c]pyridin-4(5H)one (Compound 4) and 6-amino-3-β-D-ribofuranosylimidazo[4,5-c]pyridin-4(5H)one (Compound 7) (via compounds 2 and 3 and 5 and 6, respectfully, Scheme I). Compound 4 can also be prepared in the superior process taught in Example I. The tetrahydropyranyl derivatives (Compound 8 through 13) and the 5'-deoxyribofuranosyl derivatives (Compounds 14 through 19) may also be prepared in a like manner. Examples II and III respectively, as shown in scheme I.

The 5'-phosphates may be prepared via phosphorylation of two different precursors, Scheme II. Example IV shows phosphorylation of 5(4)cyanomethyl-1-β-D-ribofuranosylimidazolo-4(5)-carboxamide and Example V, phosphorylation of compounds 4 and 7. The 3',5'-cyclic phosphates (Compounds 21 and 24) are prepared, Example VI, from Compounds 20 and 22 respectively or 24 is prepared via 21, as shown in Scheme II.

The compounds of the invention may also be blocked as shown in scheme II. Example VII shows blockage at the sugar portion (Compounds 25 and 26) blockage of the aglycon (Compound 27) or blockage of both the sugar and the aglycon (Compound 28).

α-Anomers, Scheme I compounds 2c and 5c, of the ribose sugar moiety can also be isolated as illustrated in Example VIII.

The compounds of the invention have demonstrated antiviral, antibacterial and antitumor properties. Example IX shows the antiviral efficacy of compounds 3, 4, 13, 16, 20, 22, 29 and 30. Example X demonstrates the in vitro antibacterial efficacy of compounds 7 and 30. Example XI demonstrates the in vivo antibacterial activity of compounds 7 and 23. Example XII demonstrates the antitumor properties of compound 30.

SCHEME I

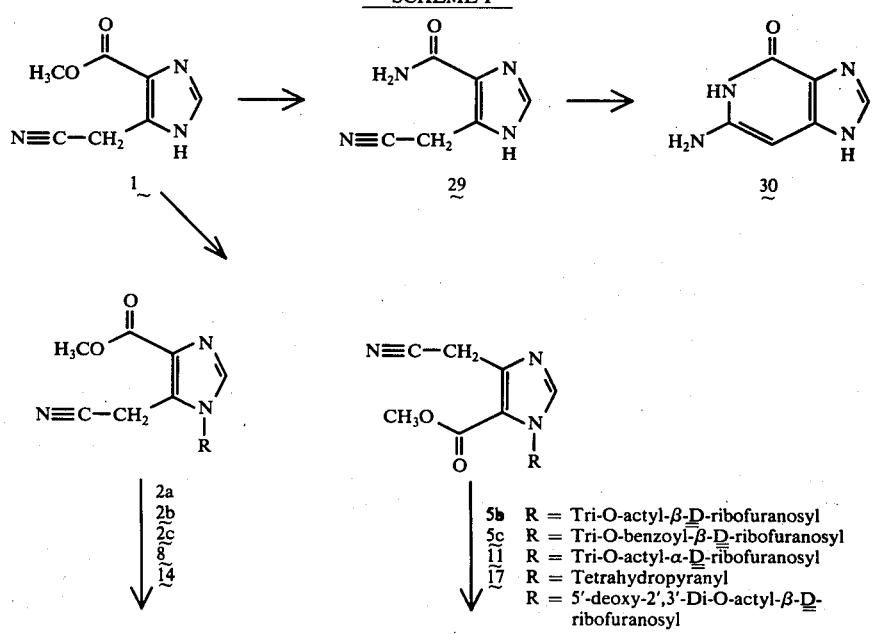

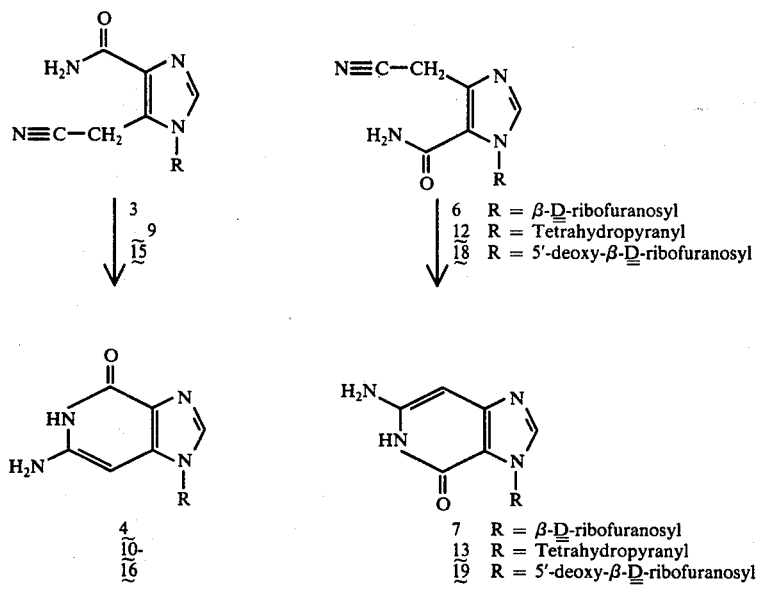
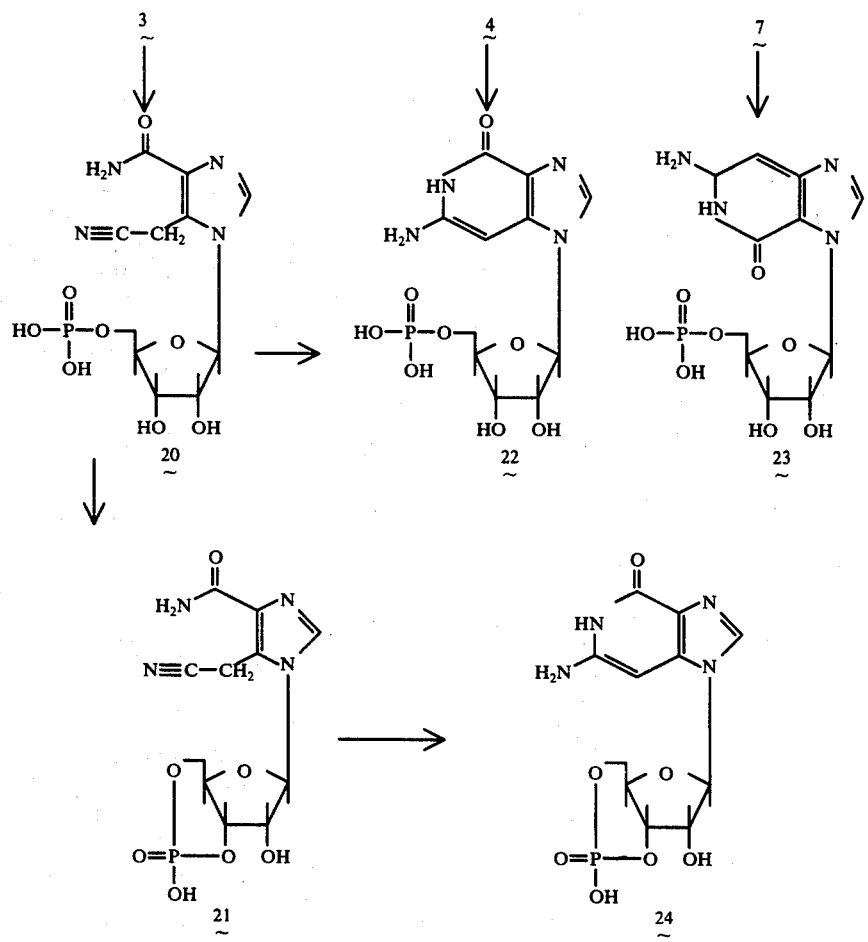
SCHEME II

-continued

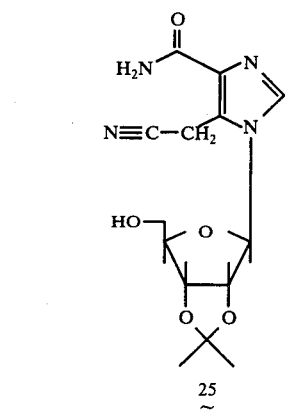

25

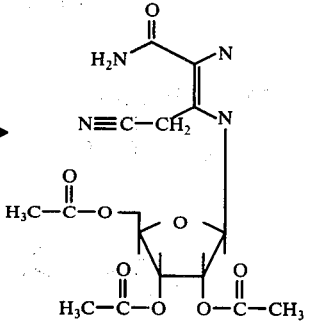

26

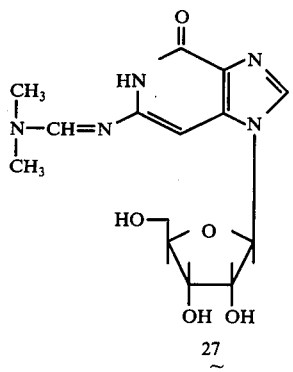

27

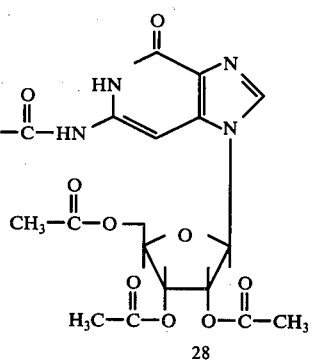

28

EXAMPLE I

Methyl 5-cyanomethyl-1-(2,3,5-tri-O-benzoyl-β-D-ribofuranosyl)imidazole-4-carboxylate (Compound 2b)

Compound 1 (25.0 g, 0.151 mol) was refluxed under anhydrous conditions for 12 hr with hexamethyldisilazane (300 ml) and ammonium sulfate (0.5 g). The excess hexamethyldisilazane was removed by distillation under reduced pressure providing the trimethylsilyl derivative as a yellowish brown oil. The oil was dissolved in dry 1,2-dichloroethane (800 ml). 1-O-Acetyl-2,3,5-tri-O-benzoyl-β-D-ribofuranose (76.5 g, 0.151 mol) was added to the solution followed by addition of stannic chloride (25.4 ml, 0.218 mol) in one portion. Some brown ppt. forms after ca. 0.5 hr stirring at ambient temperature. Tlc (silica gel, benzene-ethyl acetate, 1:1) of an ethanolyzed aliquot indicated almost complete conversion of the sugar and base to the title compound after 15 min of stirring. The reaction mixture was stirred further for 4–24 hr and then poured into a 5% sodium hydrogen carbonate solution (3 l.). The mixture was filtered thru celite, extracted with chloroform (3 × 800 ml), and the combined, dried (MgSO₄) extracts were evaporated under reduced pressure (50°) to a light beige foam (92 g, 100%). This material is of high purity and was used for further reactions. An analytical sample was obtained by passing 1 g of the foam dissolved in benzene-ethyl acetate (1:1) through a column of silica gel (10 g) packed in benzene-ethyl acetate (1:1), white foam; pmr (DMSO-d₆); δ3.85 (s,3, CH₃), 4.52 (s,2,C$\underline{H}_2$), 6.6 (d,1,J=5 Hz, $\underline{H}_{1'}$), 8.38 (s,1,C₂$\underline{H}$).

Anal. Calcd for C₃₃H₂₇N₃O₉: C, 65.02; H, 4.46; N, 6.89. Found: C, 65.19; H, 4.46; N, 6.63.

5-Cyanomethyl-1-β-D-ribofuranosylimidazole-4-carboxamide (Compound 3)

Compound 2a or 2b (0.046 mol) and liquid ammonia (150 ml) was placed in a steel bomb (300 ml). The bomb was three-quarters submerged in a steam bath and heated for 3 hr. At this point, tlc (silica gel, chloroform-methanol, 4:1) indicated a trace of the intermediate, methyl 5-cyanomethyl-1-β-D-ribofuranosylimidazole-4-carboxylate, remaining and that a small amount of Compound 4 had formed. The ammonia was allowed to evaporate at room temp and the residue was subjected to a vacuum overnight to remove the last traces of ammonia. The brown residue was dissolved in methanol, absorbed on silica gel (25 g), and placed on a column of silica gel (500 g) packed in chloroform. Elution was with chloroform-methanol (4:1). The uv absorbing fractions containing the major product were pooled and the volume was reduced by evaporation under reduced pressure until crystallization began. Crystallization was allowed to proceed overnight at 0° to provide 10.5 g (81%) of 3 as colorless needles; mp 90°–91° (after drying at 65° for 4 hr); $[\alpha]_D^{25}$ −46.9° (c,1.04, water); ir cm⁻¹ (KBr) 2250 (w) (C≡N), 1666 (s) (C=O); $\lambda_{max}^{pH\,1}$217 nm (ε8,750), 231 (sh) (8,190); $\lambda_{max}^{pH\,7}$ 217 (sh) (8,190), 232 (8,760); $\lambda_{max}^{pH\,11}$ 234 (8,750); pmr (DMSO-d₆): δ4.52 (s,2,C$\underline{H}_2$), 5.71 (d,1,J=6 Hz,$\underline{H}_{1'}$), 7.33 and 7.52 (s,1,N$\underline{H}$), 8.12 (s,1,C₂H).

Anal. Calcd for C₁₁H₁₄N₄O₅: C, 46.81; H, 5.00; N, 19.85. Found: C, 46.61; H, 5.28; N, 19.49.

6-Amino-1-β-D-ribofuranosylimidazo[4,5-c]pyridin-4(5H)-one (3-Deazaguanosine (Compound 4)

A mixture of 3 (4.64 g, 20 mmol), 5% sodium carbonate solution (50 ml), and ethanol (25 ml) was refluxed with stirring for 0.5 hr. Complete dissolution was obtained as reflux started. The colorless solution was filtered while hot. Crystallization begins ca. 0.5 hr after filtration and was allowed to proceed overnight at room temp. The crystals were filtered, washed thoroughly with water and ethanol, and dried at 100° for 8 hr to provide, 4.0 g of small, white needles. An additional 0.8 g of product of the same purity was obtained from a second crop of crystals; total yield was 4.8 g (85%); mp 225°–257° dec; $[\alpha]_D^{25} -59.3$ (C 0.97).1N NaOH); uv $\lambda_{max}^{pH\ 1}$ 284 nm ($\epsilon$13,650), 309 (sh) (6,570); $\lambda_{max}^{pH\ 7}$ 270 (10,120), 298 (8,140); $\lambda_{max}^{pH\ 11}$ 272 (10,120), 295 (sh) (8,140); prm (DMSO-d$_6$): $\delta$5.51 (d,1,J=6 Hz,$\underline{H}_{1'}$), 5.52 (s,1,C$_7\underline{H}$), 5.68 (s,2,N$\underline{H}_2$), 7.95 (s,1,C$_2\underline{H}$), 10.5 (s,1,N$\underline{H}$).

Anal. Calcd for C$_{11}$H$_{14}$N$_4$O$_5$: C, 46.81; H, 5.00; N, 19.85. Found: C, 46.74; H, 4.99; N, 19.72.

EXAMPLE II

Methyl 4-Cyanomethyl-1-(tetrahydropyran-2-yl)imidazole-5-carboxylate (Compound 11) and Methyl 5-Cyanomethyl-1-(tetrahydropyran-2-yl)-imidazole-4-carboxylate (Compound 8)

A mixture of methyl 4(5)-cyanomethylimidazole-5(4)carboxylate (12.4 g, 75.2 mmol), freshly distilled dihydropyran (15 ml), bis-(p-nitrophenyl)phosphate (75 mg), and dry ethyl acetate (250 ml) was refluxed for 10 hr. Additional dihydropyran (10 ml) and bis(p-nitrophenyl)phosphate (25 mg) was added and reflux continued for 5 hr. Complete dissolution was obtained at 3 hr of reflux. The light tan solution was evaporated in vacuo to a syrup which was dissolved in chloroform and placed on a column of silica gel (500 g) packed in chloroform. Elution with chloroform-ethyl acetate (1:1) provided 11.1 g (59%) of methyl 4-cyanomethyl-1-(tetrahydropyran-2-yl)-imidazole-5-carboxylate as a colorless syrup which crystallizes on standing at RT overnight. Recrystallization from 30°–60° ligroinether provided white rosettes, m.p. 82°–83°; ir cm$^{-1}$(KBr): 1720 (s) (C=O), 2260 (m) (C≡N); uv $\lambda_{max}^{pH\ 1}$ 222 nm ($\epsilon$ 11,020), $\lambda_{max}^{pH\ 5}$ 242 nm ($\epsilon$ 12,100), $\lambda_{max}^{pH\ 11}$ 242 nm ($\epsilon$ 12,100); pmr (DMSO-d$_6$); $\delta$ 3.88 (s,3,CH$_3$), 4.14 (s,2,C 2), 5.90 (m,1,H$_{2'}$), 8.22 (s,1,C$_2$H).

Anal. Calcd. for C$_{12}$H$_{15}$N$_3$O$_3$: C, 57.82; H, 6.07; N, 16.86. Found: C, 57.78; H, 6.26; N, 16.70.

Further elution with chloroform-acetone (1:1) provided 6.2 g (33%) of methyl 5-cyanomethyl-1-(tetrahydropyran-2-yl)imidazole-4-carboxylate as a clear syrup which crystallizes on standing at RT overnight. Recrystallization from 30°–60° ligroin-ether provided white needles, mp 98°–99°; ir cm$^{-1}$ (KBr): 1718 (s) (C=O), 2240 (w) C≡N); $\lambda_{max}^{pH\ 1}$ 220 nm ($\epsilon$ 11,080), $\lambda_{max}^{pH\ 7}$ 240 nm ($\epsilon$ 10,050), $\lambda_{max}^{pH\ 11}$ 242 nm ($\epsilon$ 9,820): pmr (DMSO-d$_6$): $\delta$ 3.85 (s,3,CH$_3$), 4.40 (s,2,CH$_2$) 5.51 (m,1,H$_{2'}$), 8.08 (s,1,C$_2$H).

Anal. Calcd. for C$_{12}$H$_{15}$N$_3$O$_3$: C, 57.82; H, 6.07; N, 16.86. Found: C, 57.78; H, 6.26; N, 16.07.

5-Cyanomethyl-1-(tetrahydropyran-2-yl)imidazole-4-carboxamide (Compound 9)

Methyl 5-cyanomethyl-1-(tetrahydropyran-2-yl)imidazole-4-carboxylate (0.60 g, 2.41 mmol) and liquid ammnonia (10ml) were placed in a steel bomb (40 ml). The bomb was three-quarters submerged in a steam bath and heated for 3 hr. At this point, tlc (chloroform-methanol, 9:1, silica gel) indicated complete conversion of the starting material to the carboxamide and a trace of 3-deaza-9-(tetrahydropryan-2-yl)guanine.

The ammonia was allowed to evaporate at room temperature and the residue was subjected to a vacuum overnight to remove the last traces of ammonia. The greenish-brown residue was recrystallized from methanol (charcoal) to provide 0.4 g (71%) of the title compound as faint yellow needles, mp 198°–199° after drying at 100° for 3 hr; ir cm$^{-1}$(KBr): 1685 (s) (C=O), 2250 (w) (C≡N), 3140 (s) and 3300 (s) (NH$_2$); pmr (DMSO-d$_6$): $\delta$ 4.50 (s,1,CH$_2$), 5.45 (m,1,H$_{2'}$), 7.35 1,NH), 7.53 (s,1,NH), 8.03 (s,1,C$_2$H).

Anal. Calcd. for C$_{11}$H$_{14}$N$_4$O$_2$: C, 56.39; H, 6.02; N, 23.91. Found: C, 56.59; H, 6.28; N, 23.91.

6-Amino-1-(tetrahydropyran-2-yl)imidazo[4,5-c]pyridin-4(5H)-one (Compound 10)

A mixture of 5-cyanomethyl-1-(tetrahydropryan-2-yl)imidazole-4-carboxamide (702 mg, 3 mmol), aqueous sodium carbonate solution (5%, 6 ml), and ethanol (10 ml) was refluxed 20 min. Complete dissolution was obtained as reflux began. The product precipitates as reflux is continued. The suspension is cooled, filtered, and the residue washed thoroughly with water and then ethanol (690 mg, 97%). Recrystallization from a large volume of ethanol-water (1:1) provided white needles, mp 268°–269° dec after drying at 100° for 5 hr; uv $\lambda_{max}^{pH\ 1}$ 285 nm ($\epsilon$ 13,450,), 313 nm (sh) ($\epsilon$ 6,950); $\lambda_{max}^{pH\ 7}$ 270 nm ($\epsilon$ 12,600), 300 nm ($\epsilon$ 9,350); $\lambda_{max}^{pH\ 11}$ 272 nm ($\epsilon$ 12,400), 295 nm ($\epsilon$ 9,130); pmr (DMSO-d$_6$-NaOD): $\delta$ 5.22 (m,1,H$_{2'}$), 5.58 (s,1,C$_6$H), 7.68 (s, 1,C$_2$H).

Anal. Calcd. for C$_{11}$H$_{14}$N$_4$O$_2$: C, 56.39; H, 6.02; N, 23.91. Found: C, 56.51; H, 6.15; N, 23.93.

6-Amino-3-(tetrahydropyran-2-yl)imidazo[4,5-c]pyridin-4(5H)-one (Compound 13)

A mixture of methyl 4-cyamomethyl-1-(tetrahydropyran-2-yl)-imidazole-5-carboxylate (2.49 g, 10 mmol) and liquid ammonia (20 ml) was placed in a steel bomb (40 ml) and heated at 100° (oil bath) for 5 hr. The ammonia was allowed to evaporate at room temperature and the residue subjected to a vacuum overnight. Recrystallization from methanol (charcoal) provided the title compound (1.1 g, 47%) as small off-white needles, mp 208° dec after drying at 100° for 2 hr; uv $\lambda_{max}^{pH\ 1}$275 nm ($\epsilon$ 12,300), 317 nm ($\epsilon$ 6,140); $\lambda_{max}^{pH\ 7}$ 257 nm ($\epsilon$ 6,800), 315 nm ($\epsilon$ 7,680); $\lambda_{max}^{pH\ 11}$ 257 nm ($\epsilon$ 6,580), 315 nm ($\epsilon$ 7,450); pmr (DMSO-d$_6$): $\delta$ 5.38 s,2,NH$_2$), 5.58 (s,1,C$_7$H), 6.05 (m1,H$_{2'}$), 8.22 (s,1,C$_2$H), 10.62 (s,1,NH).

Anal. Calcd. for C$_{11}$H$_{14}$N$_4$O$_2$: C, 56.39; H, 6.02; N, 23.91. Found: C, 56.21; H, 5.96; N, 23.77.

EXAMPLE III

Methyl 5-Cyanomethyl-1-(5-deoxy-2,3-di-O-acetyl-$\beta$-D-ribofuranosyl)imidazole-4-carboxylate (Compound 14)

Methyl 5(4)-cyanomethylimidazole-4-carboxylate (2.22 g, 13.4 mmol) was refluxed under anhydrous conditions for 12 hr wih hexamethyldisilazane (25 ml) and ammonium sulfate (50 mg). The excess hexamethyldisilazane was removed by distillation under reduced pressure, providing the trimethylsilyl derivative as a yellowish-brown oil. This was dissolved in 1,2-dichloroethane (35 ml). 5-Deoxy-1,2,3-tri-O-acetyl-$\beta$-D-ribofuranose (3.4 g, 13.4 mmol) was added to the solution, followed by addition of stannic chloride (2.25 ml, 19.3 mmol). The solution was stirred at RT for 9 hr. Sodium hydrogen carbonate solution (7%, 100 ml) was added and extracted 2x with chloroform. The dried organic layer was evaporated in vacuo and the residue dissolved in chloroform and placed on a column of silica gel (200 g, packed in chloroform). Elution with ethyl acetate provided the nucleoside (2.2 g, 45%) as a colorless syrup: uv $\lambda_{max}^{pH\ 1}$ 225 nm ($\epsilon$ 10,250), $\lambda_{max}^{pH\ 7}$ 235 nm (10,750), $\lambda_{max}^{pH\ 11}$ 238 nm ($\epsilon$ 10,250); pmr (DMSO-d$_6$): $\delta$ 1.45 (d,3,CH$_3$), 2.08, 2.13 (s,3,COCH$_3$), 3.85 (s,3,CO$_2$CH$_3$), 4.45 (s,2,CH$_2$), 6.05 (d,1,H$_{1'}$), J = 5Hz, 8.25 S,1,C$_2$H).

Anal. Calcd. for C$_{16}$H$_{19}$N$_3$O$_7$: C, 52.60; H, 5.24; N, 11.50. Found: C, 52.40; H, 5.31; N, 11.26.

5-Cyanomethyl-1-(5-deoxy-$\beta$-D-ribofuranosyl)imidazole-4-carboxamide (Compound 15)

A mixture of methyl 5-cyanomethyl-1-(5-deoxy-2,3-di-O-acetyl-$\beta$-D-ribofuranosyl)imidazole-4-carboxylate (2.20 g, 6.03 mmol) and liquid ammonia (30 ml) was placed in a steel bomb (40 ml) and heated at 100° for 7 hr. The ammonia was allowed to evaporate and the residue was subjected to a vacuum overnight to remove the last traces. The residue was absorbed on silica gel (5 g) and placed on a column of silica gel (60 g, packed in chloroform). Elution with chloroform-methanol (4:1) provided the pure product. Recrystallization from methanol provided colorless cubes (1.42 g, 88%); mp 173°–174° after drying at 100° for 3 hr; $[\alpha]_D^{25}$ −47.8 C=1, H$_2$O); uv $\lambda_{max}^{pH\ 1}$ 218 nm ($\epsilon$ 10,000), $\lambda_{max}^{pH\ 7}$ 233 nm ($\epsilon$ 10,200), $\lambda_{max}^{pH\ 11}$ 234 nm ($\epsilon$ 9,730); pmr (DMSO-d$_6$): $\delta$ 1.35 (d,3,CH$_3$), 5.66 (d,1,H$_{1'}$), J = 5 Hz, 7.45 (d,2,NH$_2$), 8.02 (s,1,C$_2$H).

Anal. Calcd. for C$_{11}$H$_{14}$N$_4$O$_4$: C, 49.62; H, 5.30; N, 21.04. Found: C, 49.44; H, 5.20; N, 20.92.

6-Amino-1-(5-deoxy-$\beta$-D-ribofuranosyl)imidazo[4,5-c]pyridine-4(5H)-one (Compound 16)

A mixture of 5-cyanomethyl-1-(5-deoxy-$\beta$-D-ribofuranosyl)imidazole-4-carboxamide (1.1 g, 4.13 mmol), aqueous sodium carbonate (5%, 7 ml), and ethanol (6 ml) was stirred under reflux for 0.75 hr, treated with charcoal, and filtered through celite. The light yellow flocculent crystals were filtered and washed with water and then ethanol. Drying at 100° for 5 hr provided 0.9 g (82%) of the product; mp > 310°; $[\alpha]_D^{25}$ −65.6 (C=1, 0.1 N NaOH); uv $\lambda_{max}^{pH\ 1}$ 284 nm ($\epsilon$ 13,000), 3.08 nm (sh ($\epsilon$ 6,920); $\lambda_{max}^{pH\ 7}$ 272 nm ($\epsilon$ 12,200), 299 nm ($\epsilon$ 9,150; $\lambda_{max}^{pH\ 11}$ 272 nm ($\epsilon$ 12,200), 295 nm (sh) ($\epsilon$ 9,150); pmr (DMSO-d$_6$): $\delta$ 1.36 (d,3,CH$_3$), J = 6Hz, 5.52 (s,1,C$_7$H), 5.55 (d,1,H$_{1'}$), J = 5Hz, 5.75 (brs,2,NH$_2$), 7.90 (s,1,C$_2$H).

Anal. Calcd. for C$_{11}$H$_{14}$N$_4$O$_4$: C, 49.62; H, 5.30; N, 21.04. Found: C, 49.66; H, 5.37; N, 21.20.

Methyl 4-Cyanomethyl-1-(2,3-di-O-acetyl-5-deoxy-$\beta$-D-ribofuranosyl)imidazole-5-carboxylate (Compound 17) and Methyl 5-Cyanomethyl-1-(2,3-di-O-acetyl-5-deoxy-$\beta$-D-ribofuranosyl)imidazole-4-carboxylate (Compound 14)

Methyl 5(4)-Cyanomethylimidazole-4(5)-carboxylate (3.0 g, 18.2 mmol) was refluxed under anhydrous conditions for 12 hr with hexamethyldisilazane (50 ml) and ammonium sulfate (25 mg). The excess hexamethyldisilazane was removed by distillation under reduced pressure, providing the trimethylsilyl derivative as a yellowish-brown oil. The oil was dissolved in dry 1,2-dichloroethane (100 ml). 5-Deoxy-1,2,3-tri-O-acetyl-D-ribofuranose (4.73 g, 18.2 mmol) was added to the solution, followed by the addition of stannic chloride (1.06 ml, 9.1 mmol) in one portion. The reaction solution was stirred at RT for 48 hr and then poured into a 7% sodium hydrogen carbonate solution (200 ml). The mixture was filtered through celite, extracted with chloroform (3×50 ml) and the combined, dried (MgSO$_4$) extracts were evaporated under reduced pressure (50°) to a colorless oil (6.6 g). Column chromatography (250 g of silica gel packed in chloroform, eluted with ethyl acetate) provided, as the first isomer off the column, methyl 4-cyanomethyl-1-(2,3-di-O-actyl-5-deoxy-$\beta$-D-ribofuranosyl)imidazole-5-carboxylate (3.2 g. 48%). Recrystallization from ethanol provided colorless needles; mp 123°–124° after drying at 65° for 5 hr; uv $\lambda_{max}^{pH\ 1}$ 234 nm ($\epsilon$ 8,430), $\lambda_{max}^{pH\ 7\ and\ 11}$ 242 nm ($\epsilon$ 11,000); pmr (DMSO-d$_6$): $\delta$ 1.45 (d,3,C$_5$·CH$_3$) J = 6Hz, 2.12, 2.15 (s,3,COCH$_3$), 3.85 (s,3,CO$_2$CH$_3$), 4.2 (s,2,CH$_2$), 6.39 (d,1,H$_{1'}$) J = 3Hz, 8.34 (s,1,C$_2$H).

Anal. Calcd. for C$_{16}$H$_{19}$N$_3$O$_7$: C, 52.60; H, 5.24; N, 11.50 Found: C, 52.32; H, 5.37; N, 11.29.

Further elution of the column with ethyl acetate provided methyl 5-cyanomethyl-1-(2,3-di-O-acetyl-5-deoxy-$\beta$-D-ribofuranosyl)imidazole-4-carboxylate (1.7 g, 26%). This material was identical to the material prepared above. (Example III).

6-Amino-3-(5-deoxy-$\beta$-D-ribofuranosyl)imidazo[4,5-c]pyridin-4(5H)-one (Compound 19)

A mixture of methyl 4-cyanomethyl-1-(2,3-di-O-acetyl-5-deoxy-$\beta$-D-ribofuranosyl)imidazole-5-carboxylate (2.6 g, 7.13 mmol) and liquid ammonia (25 ml) was heated in a steel bomb (40 ml) for 2.5 hr at 100°. The ammonia was allowed to evaporate at RT and the last trace removed by application of a vacuum overnight. The greenish-brown residue was recrystallized from water (charcoal) to provide 1.3 g (68%) of the nucleoside as light yellow microcrystals; mp dec. > 200°; $[\alpha]_D^{25}$ +29.3 (C=1.06, water); uv $\lambda_{max}^{pH\ 1}$ 277 nm $\epsilon$ 11,700), 317 nm ($\epsilon$ 5,980); $\lambda_{max}^{pH\ 7}$ 258 nm ($\epsilon$ 6,500), 317 nm ($\epsilon$ 7,530); $\lambda_{max}^{pH\ 11}$ 258 nm ($\epsilon$ 6,500), 317 nm ($\epsilon$ 7,280); pmr (DMSO-d$_6$): $\delta$ 1.35 (d,3,C$_5$·CH$_3$) J= 6Hz), 5.38 (s,2,NH$_2$), 5.5 (s,1C,$_7$H), 6.24 (d,1,H$_{1'}$) J = 4Hz, 10.62 (brs,1,NH).

Anal. Calcd. for C$_{11}$H$_{14}$N$_4$O$_4$: C, 49.62; H, 5.30; N, 21.04. Found: C, 49.42; H, 5.28; N, 20.86.

EXAMPLE IV

5-Cyanomethyl-1-$\beta$-D-ribofuranosylimidazole-4-carboxamide 5'-phosphate (Compound 20)

To a solution of phosphoryl chloride (4.9 g, 32 mmol) and trimethyl phosphate (40 ml) (cooled to 0° with an ice-bath) was added, with stirring, powdered 3 (2.26 g, 8 mmol). The suspension was stirred at 0° (protected from moisture) for 4 hr. Complete dissolution was obtained within 0.5 hr. Tlc (aliquot hydrolyzed with water, silica gel, acetonitrile-0.2M ammonium chloride, 3:1) indicated a complete and clean conversion of the nucleoside to the nucleotide. The light beige solution was added dropwise to a vigorously stirred flask of anhydrous ether (500 ml). The ether was decanted and additional ether (250 ml) was added to the residual syrup. After stirring for 10 min, the ether was decanted. This process was repeated once more with additional ether (250 ml). The residual syrup was dissolved in crushed ice (ca. 50 g) and the solution then extracted with chloroform (2 × 50 ml). The aqueous solution was allowed to stand overnight at room temp, then adjusted to pH 8 with 1 N sodium hydroxide solution and placed on a column of Bio-rad AG-1×8 (formate form, 50-100 mesh, 50 ml). The column was first washed with water (250 ml) and then with a gradient of 0.2 M to 0.5 M formic acid (1 l. each). The product appeared after ca. 1 l. of gradient had passed through the column. The product containing fractions were pooled and evaporated under reduced pressure to a small volume. Addition of ethanol (100 ml) provided the desired phosphate as a white powder (1.61 g, 53%) after wshing successively with ethanol and ether, and drying at 100° for 5 hr; mp dec > 160°; $[\alpha]_D^{25}$ − 27.5 (C 1.06, 0.1 N NaOH); $\lambda_{max}^{pH\ 1}$ 213 nm ($\epsilon$ 10,100); $\lambda_{max}^{pH\ 7}$ 235 (8,750); $\lambda_{max}^{pH\ 11}$ 238 (7,410; mpr (DMSO-d$_6$); $\delta$ 5.72 (d,1,J=4 Hz, H$_{1'}$), 8.08 (s,1,C$_2$H).

Anal. Calcd for C$_{11}$H$_{15}$N$_4$O$_8$P.H$_2$O: C, 34.74; H, 4.50; N, 14.73. Found: C, 35.21; H, 4.39; N, 14.98.

6-Amino-1-$\beta$-D-ribofuranosylimidazo[4,5-c]pyridin-4(5H)-one 5'-phosphate (3-Deaza-5'-guanylic acid, Compound 22)

A solution of 20 (1.09 g, 3 mmol) and water (50 ml) was adjusted to pH 10.0 with 10% sodium carbonate and refluxed 40 min. The light yellow solution was adjusted to pH 6.5 with Dowex 50(H+) and placed on a column of Bio-Rad AG-1×8 (formate form, 50-100 mesh, 40 ml). The column was first washed with water (250 ml) and then with a 0.2M to 0.5M formic acid gradient (1.1 each). The product appeared after ca. 1 l. of gradient had passed through the column. The fractions containing the product was pooled and evaporated to a small volume. Addition of ethanol (150 ml) precipitated a light beige powder which was filtered and washed successively with ethanol and ether to provide 0.49 g (45%) of 22 mp dec > 180° after drying at 100° for 12 hr; $[\alpha]_D^{25}$ − 11.4 (C 1.06, water); $\lambda_{max}^{pH\ 1}$ 287 nm ($\epsilon$8,400), 306 (sh) (4,930); $\lambda_{max}^{pH\ 7}$ 272 (8,400), 303 (6,380); $\lambda_{max}^{pH\ 11}$ 272 (8,130), 303 (6,090); pmr (D$_2$O): $\delta$ 5.89 (d,1,J=4 Hz H$_{1'}$), 9.00 (1,s,C$_2$H).

Anal. Calcd for C$_{11}$H$_{15}$N$_4$O$_8$P: C, 36.47; H, 4.17; N, 15.47. Found: c, 36.22; H, 4.29; N, 15.21.

EXAMPLE V

6-Amino-1-$\beta$-D-ribofuranosylimidazo[4,5-c]pyridin-4(5H)-one 5'-phosphate (3-Deaza-5'-guanylic acid, Compound 22)

To a solution of phosphoryl chloride (2.82 g. 18.44 mmol) and trimethyl phosphate (11.5 ml) (cooled to 0° with an ice-bath) was added powdered 4 (1.3 g, 4.61 mmol). The suspension was stirred at 0° (protected from moisture) for 10 hr. The amber solution was added dropwise to a vigorously stirred flask of anhydroud ether (250 ml). The ether was decanted and additional ether (150 ml) was added to the beige precipitate. After stirring for 0.5 hr the ether was decanted and this procedure was repeated once more with additional ether (150 ml). The precipitate was filtered, washed with ether, and then dissolved in ice-water (ca. 30 g). The aqueous solution was allowed to stand at room temp overnight, adjusted to pH 8 with 1N NaOH, and placed on a column of Bio-Rad Ag-1×8 (formate form, 50-100 mesh, 15 ml). After washing with water (150 ml), the column was eluted with a gradient of 0.2M to 0.5M formic acid (500 ml each, 15 ml fractions were collected). Fractions 20-75 were pooled are reduced to a small volume in vacuo. Addition of ethanol (150 ml) precipitated 22 which was filtered, washed with ethanol and ether, and dried under high vacuum at 100° for 12 hr (0.5 g, 30%).

The material was identical to 22 prepared in EXAMPLE IV.

6-Amino-3-$\beta$-D-ribofuranosylimidazo[4,5-c]pyridin-4(5H)-one-5'-phosphate (Compound 23)

A mixture of powdered 6-amino-3-$\beta$-D-ribofuranosylimidazo[4,5-c]-pyridin-4(5H)-one (564 mg, 2 mmol), phosphoryl chloride (612 g, 4 mmol), and trimethyl phosphate (10 ml) was stirred at 0° for 3 hr. Tlc (aliquot hydrolyzed with water, silica gel, isopropanol/28% ammonium hydroxide/water, 7:1:2) indicated a complete and clean conversion of the nucleoside to the nucleotide. The cold, light beige solution was added dropwise to a vigorously stirred flask of cold, anhydrous ether (250 ml). After stirring for 10 min, the ether was decanted. This process was repeated once more with additional ether (125 ml). The white precipitate was filtered, washed with ether, and then dissolved in ice water (∼ 50 g). The aqueous solution was adjusted to ca. pH 8.5 with 1 N sodium hydroxide and placed on a column of Bio-Rad Ag-1×8 (formate form, 50-100 mesh, 20 ml). After washing with water (500 ml), the column was eluted with a gradient of water (300 ml) to 1.0 M formic acid (300 ml). The fractions containing the product were pooled and evaporated in vacuo. Crystallization from ethanol-water provided the phosphate as white crystals (400 mg from two crops, 55%); mp dec. > 200° after drying at 100° for 5 hr; $[\alpha]_D^{25}$ +92.2 (C=1.05, H$_2$O); uv $\lambda_{max}^{pH\ 1}$ 277 nm ($\epsilon$ 10,720), 316 nm ($\epsilon$ 5,370); $\lambda_{max}^{pH\ 7}$ 258 nm ($\epsilon$ 5,722), 316 nm ($\epsilon$ 6,700); $\lambda_{max}^{pH\ 11}$ 258 nm ($\epsilon$ 5,722), 316 nm ($\epsilon$ 6,700); R$_f$(silica gel, isopropanol/ammonium hydroxide/water, 7:1:2) = 0.20; R$_f$(silica gel, acetonitrile/0.2 M ammonium chloride, 3:1) = 0.24.

EXAMPLE VI

5-Cyanomethyl-1-$\beta$-D-ribofuranosylimidazole-4-carboxamide-3',5'-cyclic phosphate (Compound 21)

A mixture of 5-cyanomethyl-1-$\beta$-D-ribofuranosylimidazole-4-carboxamide-5'-phosphate (1.5 g, 4.15 mmol), 4-morpholine-N,N'-dicyclohexylcarboxamide (1.22 g, 4.15 mmol), and dry pyridine (100 ml) was evaporated in vacuo. The residual syrup was co-evaporated several times with additional dry pyridine (75 ml each time). The syrup was dissolved in dry pyridine (150 ml) and added dropwise (over a 1-hr period) through a reflux condenser, into a refluxing anhydrous solution of dicyclohexylcarbodiimide (4.28 g, 20.75 mmol) in dry pyridine (300 ml). The solution was refluxed an additional 2 hr and water (50 ml) was added. After 8 hr, the solution was evaporated in vacuo and water (50 ml) and ether (50 ml) was added to the residue. The aqueous layer was separated, extracted with 2× 100 ml of ether, adjusted to ca. pH 8 with concentrated ammonium hydroxide, and placed on a Bio-Rad AG-1×8 (50-100 mesh) formate column (40 ml). The column was first washed with water (500 ml), then with a gradient of 0.75 M to 1.50 M formic acid (1 liter each). The product appeared after ca. 1 liter of gradient had passed through the column. Fractions containing the product were pooled and evaporated in vacuo to a small volume. Addition of ethanol provided the desired cyclic phosphate as a beige powder (500 mg, 35%) after washing successively with ethanol and ether, and drying at 100° for 5 hr; mp > 180°; uv $\lambda_{max}^{pH\ 1}$ 215 nm, $\lambda_{max}^{pH\ 7}$ 234 nm, $\lambda_{max}^{pH\ 11}$ 237 nm; R$_f$ (silica gel, isopropanol/ammonium hydroxide/water, 7:1:2) = 0.57, R_f (silica gel, acetonitrile/0.2 M ammonium chloride, 3:1) = 0.56.

6-Amino-1-β-D-ribofuranosylimidazo[4,5-c]pyridin-4(5H)-one-3',5'-cyclic phosphate (Compound 24)

Method A.

A solution of 5-cyanomethyl-1-β-D-ribofuranosylimidazole-4-carboxamide-3',5'-cyclic phosphate (21) (344 mg, 1 mmol) and water (25 ml) was adjusted to pH 10.0 with 10% sodium carbonate and refluxed 40 min. The yellow solution was adjusted to pH 6.5 with Dowex 50 (H+) and placed on a column of Bio-Rad AG-1×8 (formate form, 50–100 mesh, 25 ml). The column was first washed with water (250 ml) and then with a gradient of 0.75 M formic acid (1 liter) to 1.5 M formic acid (1 liter). The fractions containg the product were pooled and evaporated in vacuo to a small volume. Addition of ethanol precipitated the cyclic phosphate which was filtered, washed with ethanol and ether, and dried in vacuo at 100° for 12 hr (150 mg, 44%); mp dec. >200°; uv $\lambda_{max}^{pH\ 1}$ 285 nm, 306, nm; $\lambda_{max}^{pH\ 7}$ 271 nm, 302 nm; $\lambda_{max}^{pH\ 11}$ 271 nm, 303 nm; R_f (silica gel, isopropanol/ammonium hydroxide/water, 7:1:2) = 0.44; R_f (silica gel, acetonitrile/0.2 M ammonium chloride, 3:1) = 0.41.

Method B.

A mixture of 6-amino-1-β-D-ribofuranosylimidazo[4,5-c]-pyridin-4(5H)-one-5'-phosphate (22) (1.04 mg, 3.0 mmol), 4-morpholine-N,N'-dicyclohexylcarboxamidine (8.79 g, 3 mmol), and dry dimethyl formamide (150 ml) was evaporated in vacuo. The residual syrup was co-evaporated several times with additional dimethyl formamide (50 ml each time). The syrup was dissolved in dry dimethyl formamide (150 ml) and added dropwise (over a 1-hr period), through a reflux condenser, into a refluxing anhydrous solution of dicyclohexylcarbodiimide (3.09 g, 15 mmol) and dry pyridine (250 ml). The solution was refluxed an additional 2 hr and water (100 ml) was added. After 8 hr the solution was evaporated in vacuo and water (50 ml) and ether (50 ml) were added to the residue. The aqueous layer was separated, extracted with ether, adjusted to ca. pH 8 with concentrated ammonium hydroxide, and placed on a Bio-Rad AG-1×8 (50–100 mesh) formate column (35 ml). The column was first washed with water (500 ml) and then with a gradient of 0.75 M formic acid (1 liter) to 1.5 M formic acid (1 liter). The fractions containing the product were pooled and evaporated in vacuo to a small volume. Addition of ethanol precipitated the cyclic phosphate (412 mg, 40%). This material was identical to the cyclic phosphate prepared in Method A.

EXAMPLE VII

5-Cyanomethyl-1-(2,3-O-isopropylidene-β-D-ribofuranosyl)imidazole-4-carboxamide (Compound 25)

A solution of 5-cyanomethyl-1-β-D-ribofuranosylimidazole-4-carboxamide (3) (1.41 g, 5 mmol), dry acetone (20 ml), and 2,2-dimethoxypropane (10 ml) was cooled in an ice bath and stirred as perchloric acid (70%, 280 mg) was added. The ice bath was removed and the reaction was allowed to stir at RT for 3 hr. The reddish-orange solution was adjusted to ca. pH 7 with 10% aqueous potassium hydroxide, and evaporated in vacuo to a syrup which was dissolved in chloroform filtered and placed on a column of silica gel (45 g). Elution with chloroform-methanol (20:1) provided the isopropylidene derivative (1.35 g, 84%) as white foam; pmr (DMSO-d_6): δ 1.39, 1.58 (s,3,CH_3), 4.48 (s,2,CH_2), 6.00 (d,1,H_1'), J = 2Hz, 7.35, 7.53 (s,1,NH), 8.14 (s,1,C_2H).

Anal. Calcd. for $C_{14}H_{18}N_4O_5$: C, 57.17; H, 5.63; N, 17.38. Found: C, 57.31; H, 5.78; N, 17.49.

5-Cyanomethyl-1-(2,3,5-tri-O-acetyl-β-D-ribofuranosyl)imidazole-4-carboxamide (Compound 26)

A suspension of 5-cyanomethyl-1-β-D-ribofuranosylimidazole-4-carboxamide (1.41 g, 5 mmol), acetic anhydride (15 ml) and p-dimethylaminopyridine (20 mg) was stirred at RT for 8 hr. Tlc (silica gel, CHCl_3—MeOH, 4:1) indicated three products. Additional p-dimethylaminopyridine (20 mg) and acetic anhydride (5 ml) was added and stirring continued at RT for 36 hr. The solution was evaporated in vacuo to a syrup which was dissolved in chloroform and placed on a column of silica gel (60 g). Elution with chloroform-methanol (20:1) provided the triacetate (2.0 g, 95%) as a white foam; pmr (DMSO-d_6): δ 2.08, 2.10, 2.16 (s,3,COCH_3), 4.40 (s,2,CH_2), 6.13 (d,1,H_1'), J = 5Hz, 7.39, 7.58 (s,2,NH), 8.19 (s,1,C_2H).

Anal. Calcd. for $C_{17}H_{20}N_4O_8$: C, 50.00; H, 4.94; N, 13.72. Found: C, 49.91; H, 5.22; N, 13.36.

6-(N,N-Dimethylaminomethyleneamino)-1-β-D-ribofuranosyl)imidazo-[4,5-c]pyridin-4(5H)-one (Compound 27)

A suspension of 3-deazaguanosine (4) (564 mg, 2 mmol), dimethylformamide dimethylacetal (1.19 g, 10 mmol), and dimethyl formamide (10 ml) was heated with stirring at 80° for 6 hr. The deep red solution was evaporated in vacuo to a thin syrup and ethanol (15 ml) was added, followed by ether, until the cloud point was obtained. Cooling overnight at 0° provided 450 mg of brown microcrystals (washed with cold ethanol). An additional 200 mg of brown microcrystals of the same purity was obtained from a second crop. Total yield of the dimethylaminomethylene derivative of 3-deazaguanosine was 650 mg (96%).

An analytical sample was obtained by dissolving a portion in hot dimethyl formamide and adding ether to the cooled solution until the cloud point was obtained. Cooling at 0° overnight provided the title compound as yellow microcrystals; mp 243°–245° dec (after drying at 100° for 5 hr) $[\alpha]_D^{25}$ —78.9° (c.1, DMF); uv $\lambda_{max}^{pH\ 1}$ 275 nm (sh) (ε 13,100), 290 nm (ε 14,100); $\lambda_{max}^{pH\ 7}$ 230 nm (ε 14,100), 312 nm (ε 18,650); $\lambda_{max}^{pH\ 11}$ 233 nm (ε 13,450), 312 nm (ε 18.650); pmr (DMSO-d_6): ε 2.98 (s,3,CH_3), 3.08 (s,3,CH_3), 5.70 (d,1,H_1'), J = 6Hz, 6.15 (s,1,C_7H), 8.05 (s,1), 8.11 (s,1), 10.7 (brs,1,NH).

Anal. Calcd. for $C_{14}H_{19}N_5O_5$: C, 49.84; H, 5.68; N, 20.76. Found: C, 49.74; H, 5.72; N, 20.73.

6-Acetamido-1-(2,3,5-tri-O-acetyl-β-D-ribofuranosyl)imidazo[4,5-c]-pyridin-4(5H)-one (Compound 28)

A mixture of 3-deazaguanosine (4) (1.4 g, 4.97 mmol), acetic anhydride (13 ml), and dry pyridine (20 ml) was stirred at room temperature for 3.5 hr. The solution was evaporated in vacuo and the residue coevaporated 3× with water. Recrystallization of the residue from ethanol provided beige needles (1.5 g, 67%); mp 241°–242° dec after drying at 100° for 5 hr; uv $\lambda_{max}^{pH\ 1}$ 277 nm (ε 12,700), 297 nm (ε 13.400); $\lambda_{max}^{pH\ 7}$ 268 nm (ε 13,200), 299 nm (ε12,300); $\lambda_{max}^{pH\ 11}$ 223 nm (ε 13,700), 285 nm (ε 10,800); pmr (DMSO-d_6): δ 1.15 (s,9,COCH_3), 6.19 (d, 1,$H_{1'}$), J = 5Hz, 6.58 (s,1,$C_7H$), 8.25 (s, 1,$C_2H$), 10.70 (brs,1,NH), 11.5 (brs,1,NH).

Anal. Calcd. for $C_{19}H_{22}N_4O_9$: C, 50.66; H, 4.92; N, 12.44. Found: C, 50.62; H, 5.07; N, 12.34.

EXAMPLE VIII

Fusion of Methyl 5(4)-cyanomethylimidazole-4(5)-carboxylate (1) with 1,2,3,5-tetra-O-acetylribofuranose Methyl 5(4)-cyanomethylimidazole-4(5)-carboxylate (1) (1.65 g, 10 mmol) was thoroughly mixed with 1,2,3,5-tetra-O-acetylribofuranose (3.18 g, 10 mmol) and heated with stirring at 170° until a clear melt was obtained (ca. 1 min). Bis-(p-nitrophenyl)phosphate (20 mg) was added and heating at 170°–175° under high vacuum was continued for 25 min. The reddish-brown residue was dissolved in chloroform, extracted with 5% $NaHCO_3$, dried ($MgSO_4$), and placed on a column of silica gel (120 g packed in $CHCl_3$). Elution with EtOAc provided the following four pure nucleosides:

Methyl 4-cyanomethyl-1-(2,3,5-tri-O-acetyl-β-D-ribofuranosyl)imidazole-5-carboxylate (5a) as white needles (2.0 g 47%); m.p. 92°–93° (EtOH); $\lambda_{max}^{pH\ 7\ \&\ 11}$ 242 mμ; pmr (DMSO-$d_6$): δ 2.13 (s,9,acetyl $CH_3$'s), 3.87 (s,3,ester $CH_3$), 4.19 (s,2,$CH_2$), 6.48 (d, $J_{H_{1'}-H_{2'}}$ =3 Hz, $H_{1'}$), 8.33 (s, 1, $C_2H$).

Anal. Calcd for $C_{18}H_{21}N_3O_9$: C, 51.06; H, 5.00; H, 9.93; Found: C, 51.23; H, 5.03; N, 9.90.

Methyl 4-cyanomethyl-1-(2,3,5-tri-O-acetyl-α-D-ribofuranosyl)imidazole-5-carboxylate (5c) as a syrup (0.5 g, 11.8%); $\lambda_{max}^{pH\ 1}$ 238 mμ (ε 9,800); $\lambda_{max}^{pH\ 7\ \&\ 11}$ 247 (11,550); pmr (DMSO-$d_6$): δ 2.13 (s,9,acetyl $CH_3$'s), 3.86 (s,3,ester $CH_3$), 4.19 (s,2,$CH_2$), 6.48 (d, $J_{H_{1'}-H_{2'}}$ =5 Hz, 1, $H_1'$), 8.18 (s, 1,$C_2H$).

Anal. Calcd for $C_{18}H_{21}N_3O_9$: C, 51.06; H, 5.00; N, 9.93. Found: C, 51.32; H, 4.98; N, 9.84.

Methyl 5-cyanomethyl-1-(2,3,5-tri-O-acetyl-β-D-ribofuranosyl)imidazole-4-carboxylate (2a) as a syrup (0.8 g, 19%); this material was identical to the single isomer prepared by the stannic chloride procedure.

Methyl 5-cyanomethyl-1-(2,3,5-tri-O-acetyl-α-D-ribofuranosyl)imidazole-4-carboxylate (2c) as a syrup (0.2 g, 4.7%); $\lambda_{max}^{pH\ 1}$ 226 (ε 10,100); $\lambda_{max}^{pH\ 7}$ 236 (10,500); $\lambda_{max}^{pH\ 11}$ 238 (10,900); pmr (DMSO-$d_6$); δ 1.93, 2.04 and 2.13 (singlets, 3 protons each, acetyl $CH_3$'s), 3.84 (s,3,ester $CH_3$), 4.35 (s,2,$CH_2$), 6.49 (d, 1, $J_{H_1'-H_2'}$ = 6 Hz,1,$H_1'$), 8.03 (s,1,$C_2H$).

Anal. Calcd for $C_{18}H_{21}N_3O_9$: C, 51.06; H, 5.00; N, 9.93. Found: C, 51.28; H, 4.78; N, 9.71.

EXAMPLE IX

In this example, compounds 3, 4, 13, 16, 20, 22, 29 and 30 were tested to determine their in vitro antiviral efficacy, using the inhibition virus-induced cytopathogenic effect (CPE) method of Sidwell, et al. (Applied Microbiology 22:797–801, 1971). Briefly, the CPE procedure includes the suspension of the antiviral agent in a cell culture medium consisting of vitamins, amino acids, serum, buffer, penicillin, streptomycin and indicator dye in water. The virus suspended in the cell culture medium was added to an established monolayer of KB cells or RK-13 cells, and an equal volume of the antiviral agent was then added within 15 minutes. The infected treated cells were graded following microscopic examination. Controls for each experiment include cell controls cells and cell culture medium only), virus controls (cell and virus cell culture medium) and toxicity controls (cells and chemical and cell culture medium).

The virus rating (VR) system of Sidwell et al., described in Applied Microbiology, supra, was used to evaluate the degree of significance of CPE inhibition. A VR greater than 0.5 is indicative of significant antiviral activity and a VR of less than 0.5 suggests slight antiviral activity.

The results of the in virtro testing are shown in Table I and Table II.

TABLE I

Anti-DNA virus activity of 6-Amino-imidazo[4,5c]pyridin 4(5H)one and related compounds

| Cmpd. Number | Compound Name | AV/3 | HSV/1 | HSV/2 | VV | HCMV | MCMV | PRV | MV |
|---|---|---|---|---|---|---|---|---|---|
| 30 | 6-Amino-imidazo[4,5c]pyridin-4(5H)one | 1.1* (7)+ | 1.3 (18) | — | 1.2 (4) | 0.3 (1) | 0.6 (1) | 0.3 (1) | 0.9 (1) |
| 4 | 6-Amino-1-β-D-ribofuranosyl-imidazo[4,5c]pyridin 4(5H)one | 0.8 (4) | 0.9 (13) | — | 0.6 (7) | 0.5 (1) | — | 0.3 (1) | 1.0 (1) |
| 22 | 6-Amino-1-β-D-ribofuranosyl-imidazo[4,5c]pyridin 4(5H)one 5'-phosphate | | 0.9 (3) | 1.0 (2) | 0.7 (2) | | | | |
| 29 | 4(5)-cyanomethylimidazo-5(4) carboxamide | 0.8 (2) | 0.9 (6) | | | | | | |
| 3 | 5-cyanomethyl-1-β-D-ribofuranosylimidazo-4-carboxamide | | 0.6 (3) | 1.3 (1) | | | | | |
| 20 | 5-cyanomethyl-1-β-D-ribofuranosylimidazo-4-carboxamide 5'-phosphate | | 0.8 (2) | 0.5 (2) | 0.3 (2) | | | | |
| 13 | 6-Amino-3 (tetrahydropyran-2-yl) imidazo[4,5c]pyridin-4(5H)-one | | 0.8 (1) | | | | | | |
| 16 | 6-Amino-(5'-deoxy-β-D-ribofuranosyl)imidazo[4,5c]pyridin 4(5H)one | | 0.9 (2) | | | | | | |

*Virus Rating
+Indicates the number of tests
Virus Identification:
AV/3: adenovirus, type 3; HSV/1; herpes simplex virus, type 1; HSV/2; herpes simplex virus, type 2; VV: vaccinia virus; HCMV: human cytomegalovirus; MCMV: murine cytomegalovirus; PRV; pseudorabies virus; MV: myxoma virus.

TABLE II
Anti-RNA virus activity of 6-Amino-imidazo[4,5c]pyridin 4(5H)one and related compounds

| Cmpd Number | Compound Name | PIV/3 | PIV/1 | RV/1A | RV/2 | VIRUS RATING RV/8 | RV/13 | RV/30 | RV/56 | IV/A$_o$ | VSV |
|---|---|---|---|---|---|---|---|---|---|---|---|
| 30 | 6-Amino-imidazo[4,5c]pyridin 4(5H)one | 1.0* (9)+ | 1.0 (1) | 0.3 (3) | 1.3 (3) | 1.3 (3) | 1.2 (10) | 0.3 (3) | 1.1 (3) | 0.5 (7) | 1.3 (1) |
| 4 | 6-Amino-1-β-D-ribofuranosyl-imidazo[4,5c]pyridin 4(5H)one | 0.6 (6) | 0.6 (1) | 0.1 (2) | 1.2 (2) | 1.2 (2) | 1.0 (1) | — | 0.7 (2) | 0.1 (5) | 1.1 (1) |
| 22 | 6-Amino-1-β-D-ribofuranosyl-imidazo[4,5c]pyridin 4(5H)one 5'-phosphate | 0.8 (3) | 0.3 (1) | | | | 0.9 (3) | | | | |
| 29 | 4(5)-Cyanomethylimidazole-5(4)-carboxamide | 0.5 (4) | | | | | 0.6 (4) | | | | |

*Virus rating
+Indicating the number of tests
Virus Identification:
PIV/3: Parainfluenza virus, type 3; PIV/1: parainfluenza virus, type 1; RV/1A: rhinovirus, type 1A; RV/2: rhinovirus, type 1; RV/8: rhinovirus, type 8; RV/13: rhinovirus, type 13; RV/30: rhinovirus, type 30; RV/56: rhinovirus, type 56; IV/A$_o$: influenza virus, type A$_o$; VSV: vesicular stomatitis virus.

EXAMPLE X

In this example compounds 7 and 30 were tested to determine their in vitro antibacterial activity. Clinical isolates of pathogens were used for this example. In vitro sensitivity of these organisms were quantitatively determined by broth dilution assay. Serial dilutions were prepared in chemically defined medium in a range from 100 to 0.01 μg/ml. The minimal Inhibitory Concentration (MIC) was recorded as the highest dilution of compound which prevented visible growth of the pathogen following 24 hr incubation at 35°.

The results are shown in Table III from compounds 7 and 30.

TABLE III
IN VITRO ACTIVITY AGAINST GRAM NEGATIVE BACTERIA

| Organism | Average MIC (μg/ml) Compound 7 | Compound 30 |
|---|---|---|
| Escherichis | 0.5 | 6 |
| Salmonella | 5.0 | |
| Serratia | 5.0 | |
| Klebsiella | 8.0 | |
| Enterobacter | 10.0 | |
| Citrobacter | 5.0 | |
| Providence | 15.0 | |
| Pseudomonas | 100 | |
| Proteus | 10 | 25 |
| Shigella | 100 | |

EXAMPLE XI

In this example compounds 7 and 23 were tested along with, as a comparison, the known antibiotic Gentamycin, to determine their in vivo antibacterial activity. Experimental infections were produced in groups of 20 white mice (ICR, COX 17 to 20 g). Appropriate dilutions of the antibiotic were administered orally (OP) (Gentamycin was administered subcutaneous [SC] since it is not orally active) to mice at 1 and 5 hr after intraperitoneal challenge with *Escherichia Coli*. The mice were observed for 7 days and the therapeutic effect of the compound was recorded as % survival of treated animals. The results are shown in Table IV.

TABLE IV
IN VIVO ACTIVITY AGAINST ESCHERICHIA COLI 138*

| Challenge No. of LD$_{50}$'s** | Compound 7[1] | % SURVIVAL Compound 23[3] | Gentamycin[2] |
|---|---|---|---|
| 1 | 100 | N.T. | 100 |
| 10 | 100 | N.T. | 100 |
| 100 | 100 | N.T. | 90 |
| 1000 | 90 | 100 | 80 |
| 10,000 | 75 | N.T. | 60 |

*Ec 138: Tetracycline and Streptomycin Resistant
[1]50 mg/kg × 2, OP
[2]1 mg/kg × 2, SC
[3]100 mg/kg × 1, OP
**The LD$_{50}$ is the challenge that killed 50% of the infected mice; the LD$_{50}$ values for the pathogen were calculated by the method of Probit Analysis.

EXAMPLE XII

In this example compound 30 was tested for antitumor activity in mice. Compound 30 was found to be cytotoxic to Hela and L1210 cells in tissue culture. A $10^{-5}$ M concentration of compound 30 caused 50% inhibition of the incorporation of $^3$H-thymidine and $^3$H-uridine into the acidinsoluble fraction of L1210 cells in tissue culture. Table V shows that in the L1210 leukemia system, compound 30 (LD$_{10}$ 500 mg/kg) at a dosage (i.p. injections) of 20 mg/kg (qd, 1-9), 40 mg/kg (qd, 1-9) and 80 mg/kg (qd, 1-9) increased the life span of BDF$_1$ female mice by 32, 43 and 63 percent respectively. Ara C (cytosine arabinoside) was included as a standard.

Compound 30 at a dosage (i.p. injections) of 40 mg/kg (qd, 1-7) also provided a 75% and 93% inhibition of the growth of subcutaneous implants of adenocarcinoma 755 in C57 Blk/6 female mice.

TABLE V
ACTIVITY OF COMPOUND 30 AGAINST LEUKEMIA L1210 IN BDF$_1$ FEMALE MICE

| Treatment (i.p.) | Average Mean Survival (days) | ΔWt. (g) | T/C |
|---|---|---|---|
| Control,Saline | 8.2 | +2.2 | — |
| Compound 30 | | | |
| 20 mg/kg, qd [1-9] | 10.83 | +2.0 | 1.32 (0/6) |
| 40 mg/kg, qd [1-9] | 12.00 | +0.4 | 1.43 (1/6) |
| 80 mg/kg, qd [1-9] | 13.33 | +1.7 | 1.63 (0/6) |
| Ara C | | | |
| 40 mg/kg, qd [1-9] | 17.33 | −0.2 | 2.11 (0/6) |

All animals were inoculated (i.p) with $10^5$ leukemic cells. Treatment was started 24 hours after transplant. Figures in parenthesis denote 21 day survivors.

We claim
1. A compound of the structure

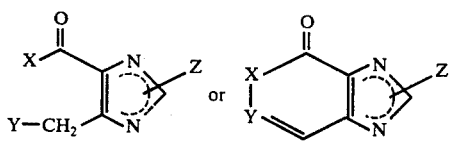

wherein X is

—NH₂ or —OCH₃; Y is

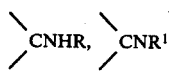

or —C≡N where R is H or acyl and R¹ is =Ch—N(CH₃)₂; Z is β-D-ribofuranosyl, 5-deoxy-β-D-ribofuranosyl, β-D-ribofuranosyl-5-phosphate, β-D-ribofuranosyl-3,5-cyclic phosphate, $C_1$–$C_{18}$ acyl and isopropylidene β-D-ribofuranosyl, $C_1$–$C_{18}$ acyl and isopropylidene 5-deoxy-β-D-ribofuranoxyl, $C_1$–$C_{18}$ acyl and isopropylidene β-D-ribofuranosyl-5-phosphate or $C_1$–$C_{18}$β-D-ribofuranosyl-3,5-cyclic phosphate; and the physiologically acceptable salts thereof; with the proviso that X is

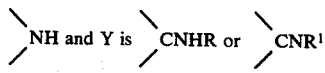

only when X and Y are joined together; and X is —NH₂ or —OCH₃ and Y is —C≡N only when X and Y are not joined together; and Z is not β-D-ribofuranosyl or $C_1$–$C_{18}$ acyl β-D-ribofuranosyl when Y is

where R is H.

2. A compound of the structure

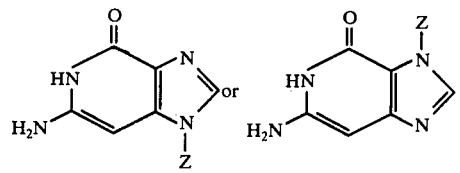

wherein Z is 5-deoxy-β-D-ribofuranosyl, β-D-ribofuranosyl-5-phosphate or β-D-ribofuranosyl-3,5-cyclic phosphate; and the $C_1$–$C_{18}$ acyl, isopropylidene and dimethylaminomethylene derivatives and the physiologically acceptable salts, thereof.

3. A compound of claim 2 wherein Z is β-D-ribofuranosyl-5-phosphate.

4. A compound of claim 2 wherein Z is 5-deoxy-β-D-ribofuranosyl.

5. A compound of claim 2 wherein Z is ribofuranosyl-3,5-cyclic phosphate.

6. A compound of claim 1 of the structure

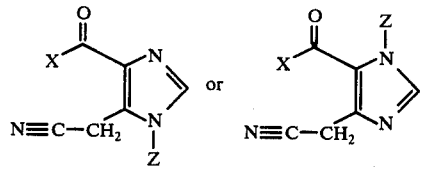

wherein X is —NH₂ or —OCH₃; Z is β-D-ribofuranosyl, 5-deoxy-β-D-ribofuranosyl, β-D-ribofuranosyl-5-phosphate, β-D-ribofuranosyl-3,5-cyclic phosphate, $C_1$–$C_{18}$ acyl and isopropylidene β-D-ribofuranosyl, $C_1$–$C_{18}$ acyl and isopropylidene 5-deoxy-β-D-ribofuranosyl-5-phosphate and $C_{1-C18}$ acyl ribofuranosyl-3,5-cyclic phosphate and the physiologically acceptable salts thereof.

7. A compound of claim 6 wherein X is NH₂ and Z is β-D-ribofuranosyl.

8. A compound of claim 6 wherein X is NH₂ and Z is β-D-ribofuranosyl-5-phosphate.

9. A compound of claim 6 wherein X is NH₂ and Z is β-D-ribofuranosyl-3,5-phosphate.

10. A compound of claim 6 wherein X is NH₂ and Z is 5-deoxy-β-D-ribofuranosyl.

11. A compound of claim 6 wherein X is OCH₃ and Z is β-D-ribofuranosyl, β-D-ribofuranosyl-5-phosphate, β-D-ribofuranosyl-3,5-cyclic phosphate, 5-deoxy-β-D-ribofuranosyl and $C_1$–$C_{18}$ acyl and isopropylidene derivatives and physiologically acceptable salts thereof.

12. 6-Amino-3-(5-phosphoryl-β-D-ribofuranosyl)imidazo[4,5-c]pyridin-4(5H)one.

13. 6-Amino-1-(5-phosphoryl-β-D-ribofuranosyl)imidazo[4,5-c]pyridin-4(5H)one.

14. 6-Amino-1-(3,5-cyclic phosphoryl-β-D-ribofuranosyl)imidazo[4,5-c]pyridin-4(5H)one.

* * * * *